United States Patent [19]

Giles

[11] 4,182,954

[45] Jan. 8, 1980

[54] METHOD AND APPARATUS FOR MEASURING MATERIAL PROPERTIES RELATED TO RADIATION ATTENUATION

[75] Inventor: Richard F. Giles, Bartlesville, Okla.

[73] Assignee: Phillips Petroleum Company, Bartlesville, Okla.

[21] Appl. No.: 898,554

[22] Filed: Apr. 21, 1978

[51] Int. Cl.$^2$ ............................................. G01N 23/00
[52] U.S. Cl. ...................................... 250/308; 250/359
[58] Field of Search ................... 250/308, 358 R, 359, 250/360

[56] References Cited

U.S. PATENT DOCUMENTS

| | | | |
|---|---|---|---|
| Re. 25,353 | 3/1963 | Foster et al. ........................ | 250/359 |
| 2,675,483 | 4/1954 | Leighton et al. ................ | 250/358 R |
| 2,979,649 | 4/1961 | Leighton ........................... | 250/358 R |
| 3,188,471 | 6/1965 | Hansen et al. ..................... | 250/308 |
| 3,202,822 | 8/1965 | Kehler ............................... | 250/266 |
| 3,210,545 | 10/1965 | Barnett ............................. | 250/358 R |
| 3,255,975 | 6/1966 | Malin et al. ...................... | 250/359 X |
| 3,435,240 | 3/1969 | Brunton ............................ | 250/559 |
| 3,460,030 | 8/1969 | Brunton et al. ............. | 250/358 R X |
| 3,500,446 | 3/1970 | Hasegawa et al. ................. | 250/308 |
| 3,619,613 | 11/1971 | Chope ............................... | 250/359 |
| 3,889,121 | 6/1975 | Bossen ............................ | 250/308 X |
| 4,001,589 | 1/1977 | Arima et al. ................ | 250/358 R X |
| 4,090,074 | 5/1978 | Watt et al. .................. | 250/358 R X |

Primary Examiner—Davis L. Willis

[57] ABSTRACT

At least one radioactive source emitting at least two types of radiation is used with two detectors to measure properties of a material which are related to radiation attenuation by that material.

18 Claims, 2 Drawing Figures

METHOD AND APPARATUS FOR MEASURING MATERIAL PROPERTIES RELATED TO RADIATION ATTENUATION

FIELD OF THE INVENTION

This invention relates to a method of measuring properties of a material which are related to the attenuation of radiation by that material. In another aspect, it relates to an apparatus for measuring those properties.

BACKGROUND OF THE INVENTION

In the manufacture of a non-woven web, it is important to be able to determine certain properties continuously or intermittently. For example, it may be necessary to determine the thickness, mass, and/or density of the material at various stages of the manufacture of the web. Such measurement is also useful in other areas, such as in the food and paper industries.

It is well known that beta particles will be absorbed in a material as a function of the thickness or density of that material. The absorption is described by the Beer-Lambert Law, which is discussed below. In the prior art, certain pure beta ray emitters have been used to measure the thickness of certain materials. However, to make such measurements, a beta plus gamma emitter has not been used with two detectors, one of which detects a first type of radiation (for example, gamma radiation) and the other of which detects that first type and a second type (for example, beta radiation). It is desirable to be able to use a beta plus gamma emitter, for example Eu-154, to make measurements of density or thickness of material because such a beta plus gamma emitter emits relatively high energy beta rays and has a long half-life and, hence, can be used in measuring relatively dense materials and can be used without frequent source replacement.

The present invention enables one to use, for example, a beta plus gamma emitter for measuring mass, density, or thickness of materials including for example, a fabric made from polypropylene fibers, heavy gauge plastic film, paper, films of food, and certain light gauge metals (foils).

It is an object of this invention to measure the thickness and/or density of a material. Another object of this invention is to provide an apparatus for making such measurements.

STATEMENT OF THE INVENTION

According to the invention, properties of a material related to the attenuation of radiation by that material are measured by (1) passing radiation emitted by a source through said material, said radiation comprising at least two different types (a first type and a second type) of radiation, (2) detecting said first type and said second type of radiation which passed through said material with a first detector which detects both said first type and said second type of radiation, (3) detecting said first type of radiation which has passed through said material with a second detector which detects said first type but not said second type of radiation, and (4) combining the detections of said detectors to obtain a measure of said second type of radiation which has penetrated said material. In one embodiment, according to the invention, the first type of radiation is gamma radiation and the second type is beta radiation. Also, according to the invention, in another embodiment, shielding is used to achieve the differential sensitivities of the two detectors. In an embodiment, a plurality of sources acting as one source is used as the source. In another embodiment, the thickness or density of a material is measured. Also, according to the invention, an apparatus employing the above method is constructed. Further, according to the invention, in one embodiment, that apparatus is used with a tachometer and a conveyor to provide a device for measuring thickness (or density).

As is known in the art, thickness measurements of materials can be made by radiation absorption techniques based on the Beer-Lambert law which is expressed as follows:

$$I = I_0 e^{-\mu x}$$

where e is the natural logarithm base, $\mu$ is the absorption coefficient (which is a function of the radiation energy from the source and of the type of material being measured), x is the thickness of the material being measured in centimeters, $I_0$ is the intensity of radiation reaching the radiation detector in the absence of the absorbing material, and I is the intensity of the radiation reaching the detector in the presence of radiation absorbing material.

Rewriting the above equation and taking the natural logarithm of both sides of the equation, one obtains $$\ln I/I_0 = -\mu x.$$

For the given material, using several known values of thickness x, one measures the corresponding values of intensity I of radiation, $I_0$ is intensity measured wherein essentially no absorber is present between the source and detectors. Then, plotting $\ln I/I_0$ versus the corresponding values of x, one obtains a straight line (the slope of which is $-\mu$). The graph can then be used to find an unknown thickness x (of that given material) for which I has been measured. Alternatively, in a similar manner a measure of the density of a material can be obtained by placing several samples having known density (in mass per unit area) between the detectors and source(s) and measuring the corresponding value of I. Again, plotting $\ln I/I_0$ versus the corresponding value of density, one obtains a straight line from which an unknown density can be found.

PREFERRED EMBODIMENTS OF THE INVENTION

Figures 1, 2:
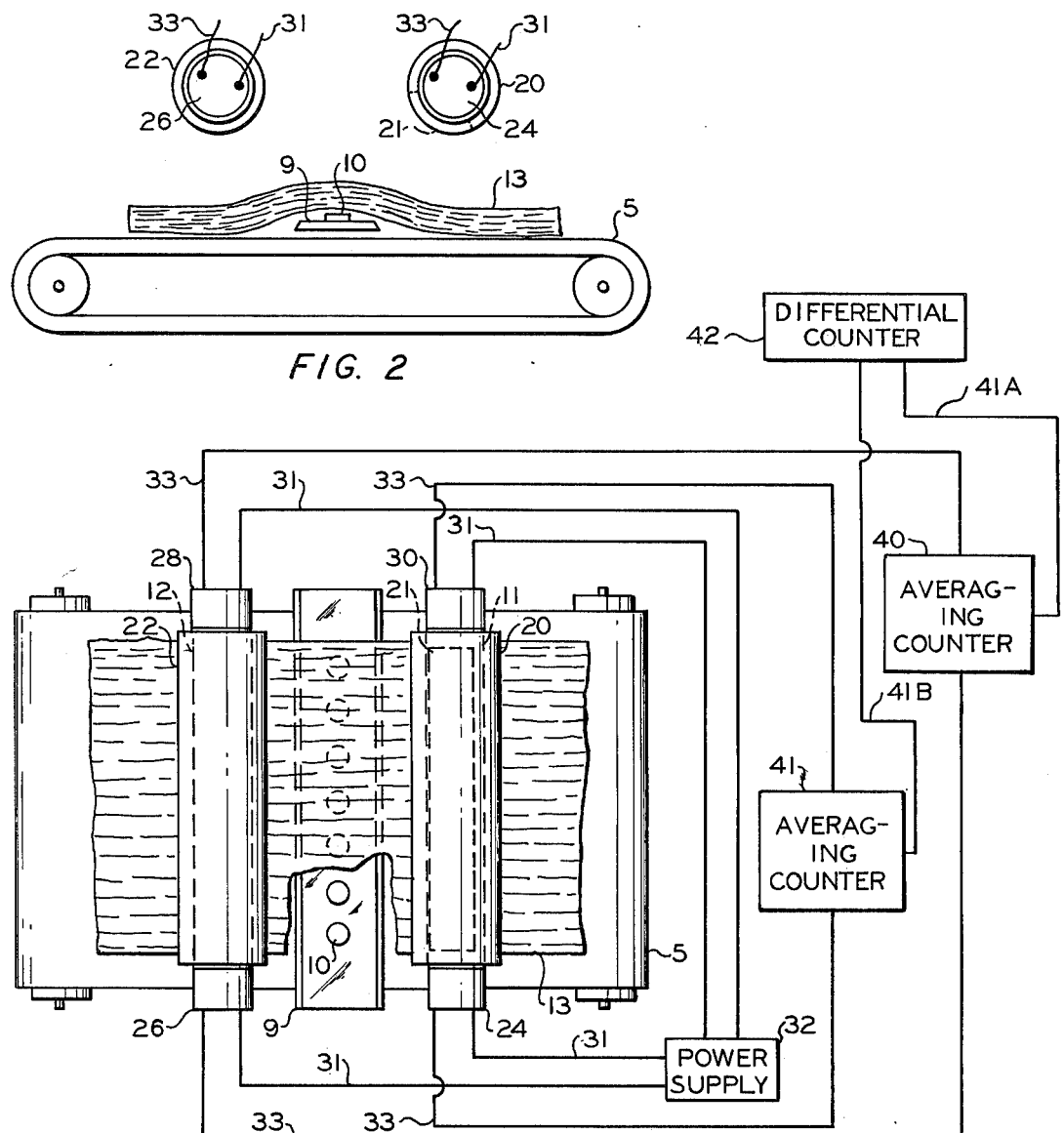
FIG. 1 is a diagrammatic plan view showing the relative location of source (or sources), detectors, and sample (material to be measured) in one embodiment of the invention.
FIG. 2 is an elevational view of FIG. 1.

Although the following description is written particularly in terms of using a radiation source or a plurality of radiation sources each of which emits both beta and gamma radiation, a source which emits any two (or more) types of radiation having different penetrating abilities, for example, beta and alpha radiation, can be used to measure material properties related to attenuation of radiation by that material. Alternatively, a plurality of such sources can be used.

Although the following is written particularly in terms of using shielding to accomplish the differential detecting by the two detectors, differential sensitivity to two different types of radiation can satisfactorily be accomplished by alternative means, for example, by using one detector which is sensitive to only a first type of radiation and by using a second detector which is sensitive to both the first type and a second type of radiation.

For reasons of convenience in the replacement of sources and in reducing the need for other correction for source decay, a source should be chosen such that its half-life is relatively long. Furthermore, the penetrating ability of the type of radiation emitted by the source should be of suitable magnitude for obtaining an accurate measure of the material property which is to be measured. For example, Europium-154 (Eu-154), which has a half-life of 16 years, is a suitable source for measuring a non-woven web with density from about 30 to about 40 oz/sq. yd. Using a plurality of small sources (each of which emit both beta and gamma radiation) is preferred to using one long source in an industrial environment because the small sources emit less radiation than would one long source used to accomplish the same function. Such suitable small nuclear radiation sources can be purchased from Oak Ridge National Laboratory, for example, in the form of flat, circular sources.

In the practice of the invention, two detectors are used. In one embodiment, one detector, called the primary detector, is at least partially unshielded so that it detects beta and gamma radiation; whereas the second detector, called the secondary detector, is shielded so that it detects gamma radiation from the source(s) but essentially none of the beta radiation.

When shielding is used, the type and amount of shielding used with the secondary detector should be selected so that the above-described shielding of the secondary detector will be accomplished. It has been found that a layer of steel 0.065 in. thick, for example, will screen out all beta radiation but essentially none of the gamma radiation.

DESCRIPTION OF THE DRAWINGS

Referring to the drawing, FIG. 1 (illustrating one embodiment) shows a conveyor 5 above which (on support 9) radiation sources 10 are located. Between sources 10 and the plane formed by the axes of primary detector 11 and secondary detector 12, the material to be measured 13 is passed. Enclosing primary detector 11 is slotted tube 20, which has a slot 21 through which both beta and gamma radiation can pass. Enclosing secondary detector 12 is tube 22, which acts as a shield against beta radiation. Photomultiplier tube 24 is located at one end of primary detector 11, and photomultiplier tube 26 is located at one end of secondary detector 12; photomutiplier tube 28 is located at the other end of secondary detector 12, and photomultiplier tube 30 is located at the other end of primary detector 11. Each photomultiplier tube 24, 26, 28, 30 is connected by a wire 31 to a power supply 32. Output wires 33 from photomultiplier tubes 26 and 28 (which are used with secondary detector 12) are suitably connected to averaging counter 40 in a frequency counting mode, which counter counts the number of pulses obtained from photomultiplier tubes 26 and 28 in a given time period and divides that number by two, thereby providing an average signal for the gamma radiation which was detected in that time period by the secondary detector 12. Likewise, the two outputs from primary detector 11 are suitably connected to averaging counter 41 in a frequency counting mode, which counter counts the number of pulses obtained from photomultiplier tubes 24 and 30 in a given time period and divides that number by two, thereby providing an average signal for beta and gamma radiation which was detected by the primary detector 11 in that time period. The digital outputs from averaging counters 40 and 41 are suitably connected by wires 41A and 41B, respectively, to differential counter 42 in a digital counting mode so that differential counter 42 combines the digital signals from averaging counters 40 and 41 to provide a differential digital signal representative of the beta radiation which was detected in that time period. The digital readout from differential counter 42 is representative of the thickness or density of the material being measured.

Referring to the drawing, FIG. 2 shows anoter view of the embodiment of the shielding arrangement which was illustrated in FIG. 1. The parts are numbered correspondingly.

The type and amount of shielding material used in making slotted tube 20 should be preferably the same as that used to make tube 22 so that (except for the presence or absence of the slot 21) the detectors can be as alike as possible.

The type of detector used in the practice of the invention can be any detector suitable for accomplishing the above-described purpose, for example, scintillation detectors. Suitable scintillation detectors which can be purchased from Nuclear Enterprises, Inc. are, for example, Model NE 102 Plastic, having a length of 24 inches and a diameter of 1 inch. In the embodiment wherein shielding is used, the two detectors can be otherwise substantially identical; then calculations will be simplified.

As shown in FIG. 1 and FIG. 2, in one embodiment, the material 13 to be measured (for example, a non-woven web) is passed between the stationary nuclear radiation source(s) 10 and the plane formed by the axes of the primary scintillation detector 11 and the secondary scintillation detector 12. For convenience, in handling the material, the material 13 to be measured can be carried on conveyor 5, and the two detectors 11 and 12 and the nuclear radiation source(s) 10 can be stationary with respect to the moving material. However, the converse (wherein the source and detectors move with respect to the material which can be stationary) is also within the scope of this invention. It is also within the scope of this invention to have the material being measured and the source and detectors all be stationary relative to each other.

It is important that the distance between the nuclear radiation source(s) 10 and the primary detector 11 be constant over time so that the same level of radiation is continuously detected; then, the calculations of thickness are simplified. Likewise, the distance between the source(s) 10 and the secondary detector 12 should be constant over time for the same reason.

When a plurality of small flat source(s) 10 is used as shown in FIG. 1, these sources are supported on a support 9 made for example of a strip of mild steel and are preferably placed in a straight line adjacent to the material 13 to be measured with length equal to the length of the detectors and equal to the width of the material to be measured. When scintillation counters are used as the detectors, the two scintillators 11 and 12 are preferably placed adjacent to each other (as shown in FIG. 1 and in FIG. 2) so that their axes are parallel and so that their respective first ends are in one plane and their respective second ends are in another plane. The plane formed by the axes of the two parallel scintillators is then preferably placed parallel to the line of small radiation source(s) 10, so that the two scintillators 11 and 12 and the line of nuclear radiation source(s) 10 are all mutually parallel. (See FIG. 1). Such positioning is preferred so that maximum detecting use is made of the source activity and so that the calculations can be simplified. The material to be measured is located between the source(s) and the plane formed by the axes of the two detectors, as shown in FIG. 2.

Once the scintillation detectors 11 and 12 and the nuclear radiation source(s) 10 have been placed in their positions, they are preferably anchored in position by suitable anchoring and supporting means (not shown).

Means for converting the radiation detected by the detectors to separate electrical signals will generally be used with he apparatus described above. When the detectors are scintillation rods, this is accomplished, for example, by using photomultiplier tubes 24, 26, 28 and 30, one photomultiplier being connected at each end of each detector. (See FIG. 1.) This arrangement is preferred to using only one photomultiplier tube with each detector because the information received from two photomultipliers provides an averaging effect which would not be contained in information received from using only one photomultiplier for each detector; and the use of two photomultiplier tubes for each detector also provides some correction for light intensity losses and time-of-travel effects which occur when light pulses are generated in one end of a scintillator rod and detected at the other end. Each photomultiplier tube has its own housing. Suitable photomultiplier tubes and housing are, for example, EMI/GENCOM Inc., (Plainview, N.Y.) Models 9824B and RFI/QL-30, respectively, operating at 1200 volts DC.

When photomultiplier tubes 24 and 30 are used with the primary detector 11, they should preferably be substantially identical to those photomultiplier tubes 26 and 28 used with the secondary detector 12 so that the electrical signals from the two detectors 11 and 12 correspond to the same scale of intensity so that when the component of the electrical signal due to gamma radiation is combined with the signal due to beta plus gamma radiation, the magnitude of the electrical signal which is present in output wire 43 is an accurate measure of the intensity of the beta radiation detected by the primary detector 11.

Each of the photomultiplier tubes 24, 26, 28, and 30 has an input wire 31 (from power supply 32) and an output wire 33. The output signals from both photomultipliers 24 and 30 associated with the primary detector 11 are averaged in an averaging counter 41, supplying the primary signal; and the output signals from photomultipliers 26 and 28 are averaged in an averaging counter 40, supplying the secondary signal. The term "averaging counter" is used herein to mean an electronic digital counter of electrical current pulses which sums the number of pulses from two photomultipliers for a given period of time and then divides that sum by two. An example of a suitable averaging counter for use in the present invention is a Hewlett Packard Electronic Counter, 500 MHz, Model 5345A.

The power supply 32 can be any suitable power supply, for example, a Spellman H-V Electronics Corporation, Model WRM 1.5 P10KD having a variable output 1000-2000 volts DC. The power supply should be compatible with the operating voltage of the photomultiplier tubes.

When scintillation detectors and photomultipliers are used, ambient light must be excluded from the photomultiplier tubes which are used with the scintillation detectors because photomultiplier tubes are extremely sensitive to light. Using optical shielding on the scintillation detectors to prevent transmission of ambient light to the photomultiplier tubes to solve this problem requires using negligible amounts of mass because any mass present appears as a bias in the basic measurement. Further, small amounts of shielding mass have major effects on the range and resolution of the instrument. One feasible alternative to using optical shielding with the photomultiplier tubes is to exclude ambient light from the entire system, for example, by operating the apparatus in a dark room. Other alternatives which may be apparent to one with ordinary skill in the art can also be used here.

When Eu-154 is used as the source, the effect of source decay can be easily removed by recalibrating the instrument periodically (for example, yearly). This calibration is done by measuring for several known values of thickness or density the corresponding values of intensity. These values are then graphed, as described above in the discussion of the Beer-Lambert law.

In the practice of the invention, a combining means, for example, a differential counter 42 which combines the averaged electrical signal supplied by the photomultiplier tubes 26 and 28 (which are associated with the secondary detector 12) with the averaged electrical signal supplied by the photomultiplier tubes 24 and 30 (which are associated with the primary detector 11) will generally be used with the apparatus described above (connected as shown in FIG. 1) so that an electrical digital signal due only to beta radiation remains. The term "differential counter" is used herein to mean an electronic digital processor of electronic pulses which (for a given period of time) combines two signals which have been obtained during that period of time and provides the difference between these two signals. The most straightforward way that the difference between the primary signal and the secondary signal can be obtained is to use a differential counter 42 which subtracts the secondary signal from the primary signal. An example of a suitable differential counter 42 is a Hewlett Packard Electronic Counter, 500 MHz, Model 5345A. The electrical digital output from differential counter 42 is representative of the thickness of the material being measured.

From the magnitude of the above-described electrical output, which is a measure of the intensity of the beta radiation which penetrated the particular material 13 being measured in the period of time during which the source activity was being detected, one can then apply the Beer-Lambert law, as described above, to obtain a measure of the average thickness or density of the material 13 that was present between the source(s) 10 and the detectors 11 and 12 in the period of time during which the source activity was being detected.

The above-described apparatus and method can be operated in cooperation with any suitable conveyor means and any suitable velocity measuring means, for example, a tachometer (not shown). For example, in measuring a fabric web which is in motion relative to the source and detectors, a velocity measuring means, for example a toothed wheel tachometer, can be placed in the web to give a measure of the velocity of the web.

By coordinating the velocity with the density measurement (in mass per unit area) found in a given amount of time, the mass flow rate or the feed rate of the equipment can be determined.

A mass measurement system similar to the embodiment shown in FIG. 2 was constructed with the following components. It was designed for measuring the thickness of a polypropylene fiber feed mat 24 inches wide and several inches thick. An array of ten Europium-154 (Eu-154) sources, with 0.1 microcuries ($\mu$C) activity each, was mounted in a straight line 2.25 inches (5.7 cm) apart on a mild steel support plate across the width of the mat and located below it. Above the mat, symmetrical with respect to and parallel to the array of sources, were located two 13-inch long, 1-inch diameter scintillator rods (Nuclear Enterprises, Inc., Model NE 102 Plastic). A photomultiplier tube (EMI/GENCOM Model 9824B) with housing (Model RFI/QL-30) was provided at each end of each of the scintillator rods to detect the resulting light pulses and was operated at 1200 volts DC. The necessary shielding to screen out beta radiation from the gamma-ray detector was provided by housing each of the scintillator rods in a length of 1.5-inch diameter x 0.0625-inch wall steel tubing and by providing one length of tubing with a 1.125-inch wide slot running the full length of its bottom to permit detection of both beta- and gamma- rays. The shield of the other tube was left solid to provide sensitivity to gamma-rays only.

In experimental runs made using this system, and also including suitable signal processing units, it was found that it is essential that ambient light be excluded if accurate measurements are to be made. Some techniques which have been tried for light shielding include the following:

(1) Wrapping the scintillator rod in a double layer of very light (0.075 oz/sq. yd.) aluminized polycarbonate film;
(2) Wrapping the scintillator rod with one layer of aluminized film and one layer of heavier (2.5 oz/sq. yd.) opaque, black paper;
(3) Painting the rod with several coats of black ultra-flat paint; and
(4) Covering the rod with black "shrink-fit" tubing.

The aluminized film is so delicate that the unavoidable handling involved with wrapping and mounting the scintillator rod invariably caused cracks in the metal film and produced light leaks. The paint and "shrink-fit" tubing both involved a large number of pinholes which could not be detected by the naked eye. The technique of wrapping the rod with one layer of aluminized film and one layer of opaque paper appeared to provide a suitably light-tight shield, but the amount of shielding mass involved in this approach so severely restricted the resolution of the instrument that it was commercially unacceptable.

It is possible that one might be able to vacuum deposit an aluminum coating directly on the scintillator rod. However, the competing goals of complete opacity to visible light and minimal mass would require very close control of the deposition process. A further complication is introduced by the physical size of the scintillator rods.

The invention is intended to cover reasonable additions and modifications in the description given above which would be apparent to one with ordinary skill in the art.

What is claimed is:

1. An apparatus for measuring properties of a material related to the attenuation of radiation by said material comprising:
   (a) a primary detector detecting a first type and a second type of radiation and producing first, pulsed signals, the number of which is representative of the intensity of said first type and said second type of radiation;
   (b) a secondary detector detecting said first type of radiation but not detecting said second type of radiation and producing second pulsed signals, the number of which is representative of the intensity of said first type of radiation;
   (c) at least one nuclear radiation source which emits both said first type and said second type of radiation and which lies spaced apart from said detectors so that said material can be oriented between said source and said detectors; and
   (d) means for combining the pulsed signals produced by said detectors to obtain a measure of the intensity of said second type of radiation which has penetrated said material.

2. An apparatus according to claim 1 wherein said first type of radiation is gamma radiation and wherein said second type of radiation is beta radiation.

3. An apparatus according to claim 2 wherein said primary detector is at least partially unshielded and can detect both beta and gamma radiation and wherein said secondary detector is shielded from beta radiation but not from gamma radiation and can detect gamma radiation.

4. An apparatus according to claim 3 wherein said detectors are scintillation detectors.

5. An apparatus according to claim 4 wherein each of said scintillation detectors is operated in cooperation with two photomultipliers.

6. An apparatus according to claim 5 wherein said nuclear radiation source is Eu-154.

7. An apparatus according to claim 6 wherein said nuclear radiation source is a plurality of small sources of Eu-154.

8. An apparatus according to claim 5 wherein said means for combining the pulsed signals produced by said detectors comprises two averaging counters and a differential counter, operable in cooperation with said detectors and with said photomultipliers, one of said averaging counters being used to average the pulsed signals from the two photomultiplier tubes which are operated in cooperation with said primary detector, thereby producing the primary signal, and the other of said averaging counters being used to average the pulsed signals from the two photomultiplier tubes which are operated in cooperation with said secondary detector, thereby producing the secondary signal, and said differential counter being used to obtain the difference between said primary signal and said secondary signal.

9. An apparatus for measuring the density of a material comprising the apparatus according to claim 8 with the additional components of (a) a conveyor means on which material to be measured is conveyed and (b) a toothed wheel suitable for being inserted into said material, said toothed wheel operating in cooperation with (c) a velocity measuring means.

10. A method for measuring material properties related to the attenuation of radiation by that material comprising:

(a) passing radiation emitted by at least one source through said material, said radiation comprising at least two different types (a first type and a second type) of radiation;
(b) detecting said first type of radiation which passed through said material with a first detector which detects said first type of radiation but which does not detect said second type of radiation;
(c) detecting said first type and said second type of radiation which have passed through said material with a second detector which detects both said first type and said second type of radiation; and
(d) combining the detections of said detectors to obtain a measure of the intensity I of said second type of radiation which has penetrated said material.

11. A method according to claim 10 wherein said first type of radiation is gamma radiation and wherein said second type of radiation is beta radiation.

12. A method according to claim 11 wherein said primary detector is at least partially unshielded and can detect both beta and gamma radiation and wherein said secondary detector is shielded from beta radiation but not from gamma radiation and can detect beta radiation.

13. A method according to claim 12 wherein said detectors are scintillation detectors.

14. A method according to claim 13 wherein each of said scintillation detectors is operated in cooperation with two photomultipliers.

15. A method according to claim 14 wherein said nuclear radiation source is Eu-154.

16. A method according to claim 15 wherein said nuclear radiation source is a plurality of small sources.

17. A method according to claim 10 and including the additional step of using the measured value of intensity I to find the thickness of said material.

18. A method according to claim 10 and including the additional step of using the measured value of intensity I to find the density of said material.

* * * * *